United States Patent [19]

Seiyama et al.

[11] Patent Number: 4,610,867

[45] Date of Patent: Sep. 9, 1986

[54] MATERIAL OF OXYGEN ION CONDUCTOR

[75] Inventors: Tetsuro Seiyama; Hiromichi Arai; Toshiya Kunisaki, all of Fukuoka, Japan

[73] Assignee: Yazaki Corporation, Tokyo, Japan

[21] Appl. No.: 722,790

[22] Filed: Apr. 12, 1985

[30] Foreign Application Priority Data

Oct. 22, 1984 [JP] Japan .................. 59-220520

[51] Int. Cl.$^4$ .................. C01F 11/02; C01F 17/00
[52] U.S. Cl. .................. 423/635; 423/625; 423/636; 73/23; 204/421; 204/424; 436/136; 422/98
[58] Field of Search ............... 423/635, 593, 625, 636; 422/98, 90; 436/82, 136, 137; 429/218; 73/23; 204/421, 424, 427

[56] References Cited

U.S. PATENT DOCUMENTS

| | | |
|---|---|---|
| 3,837,808 | 9/1974 | Sugimoto et al. .................. 436/136 |
| 3,948,813 | 4/1976 | Holcombe, Jr. et al. ........... 423/593 |
| 4,169,708 | 10/1979 | Muggli .................. 436/136 |
| 4,225,559 | 9/1980 | Achari et al. .................. 436/137 |
| 4,233,033 | 11/1980 | Eifler et al. .................. 436/137 |
| 4,283,256 | 8/1981 | Howard et al. .................. 436/137 |
| 4,298,573 | 11/1981 | Fujishiro .................. 436/137 |
| 4,454,494 | 6/1984 | Williams et al. .................. 422/98 |
| 4,505,803 | 3/1985 | Mase et al. .................. 422/98 |
| 4,532,492 | 7/1985 | Esper et al. .................. 422/98 |
| 4,535,316 | 8/1985 | Wertheimer et al. .................. 422/98 |

Primary Examiner—Andrew H. Metz
Assistant Examiner—Anthony McFarlane
Attorney, Agent, or Firm—Ladas & Parry

[57] ABSTRACT

Materials of oxygen ion conductors comprising $CeO_2$-$CaO$ type oxides wherein 5–60 mol % of CaO is mixed with $CeO_2$ having a fluorite structure, and composite oxides wherein $CeO_2$ of said $CeO_2$-$CaO$ type oxides is replaced by oxide of magnesium or aluminum by 5–10 mol %.

7 Claims, 11 Drawing Figures o : $(CeO_2)_{0.90}(CaO)_{0.10}$
▲ : $(CeO_2)_{0.80}(CaO)_{0.20}$
□ : $(CeO_2)_{0.70}(CaO)_{0.30}$
● : $(CeO_2)_{0.60}(CaO)_{0.40}$
▲ : $(CeO_2)_{0.50}(CaO)_{0.50}$
◆ : $(CeO_2)_{0.40}(CaO)_{0.60}$
■ : $(CeO_2)_{0.20}(CaO)_{0.80}$
○ : $(ZrO_2)_{0.85}(CaO)_{0.15}$
◉ : $CeO_2$ (●: Zr ATOM  ○: O ATOM)

OXIDES ADDED (mol %)

1 : $(Y_2O_3)_{0.1}(ZrO_2)_{0.9}$    2 : $(Sc_2O_3)_{0.1}(ZrO_2)_{0.9}$
3 : $(CaO)_{0.13}(ZrO_2)_{0.87}$    4 : $(Y_2O_3)_{0.07}(ThO_2)_{0.93}$
5 : $(Gd_2O_3)_{0.2}(CeO_2)_{0.8}$    6 : $(CaO)_{0.12}(HfO_2)_{0.88}$
7 : $(Y_2O_3)_{0.25}(Bi_2O_3)_{0.75}$    8 : $(WO_3)_{0.25}(Bi_2O_3)_{0.75}$
9 : $(SrO)_{0.05}(La_2O_3)_{0.95}$    10 : $La_{0.7}Ca_{0.3}AlO_{2.65}$
11 : $CaTi_{0.7}Al_{0.3}O_{2.85}$    12 : $LaO_{0.97}F_{1.06}$
13 : $LaO_{1.00}F_{1.00}$

1: CSZ  2: YDT  3: $(Y_2O_3)_{0.05}(CeO_2)_{0.95}$
4: $(CaO)_{0.15}(La_2O_3)_{0.85}$  5: $(Y_2O_3)_{0.27}(Bi_2O_3)_{0.73}$
6: $(Y_2O_3)_{0.5}(TiO_2)_{0.5}$  7: AgI

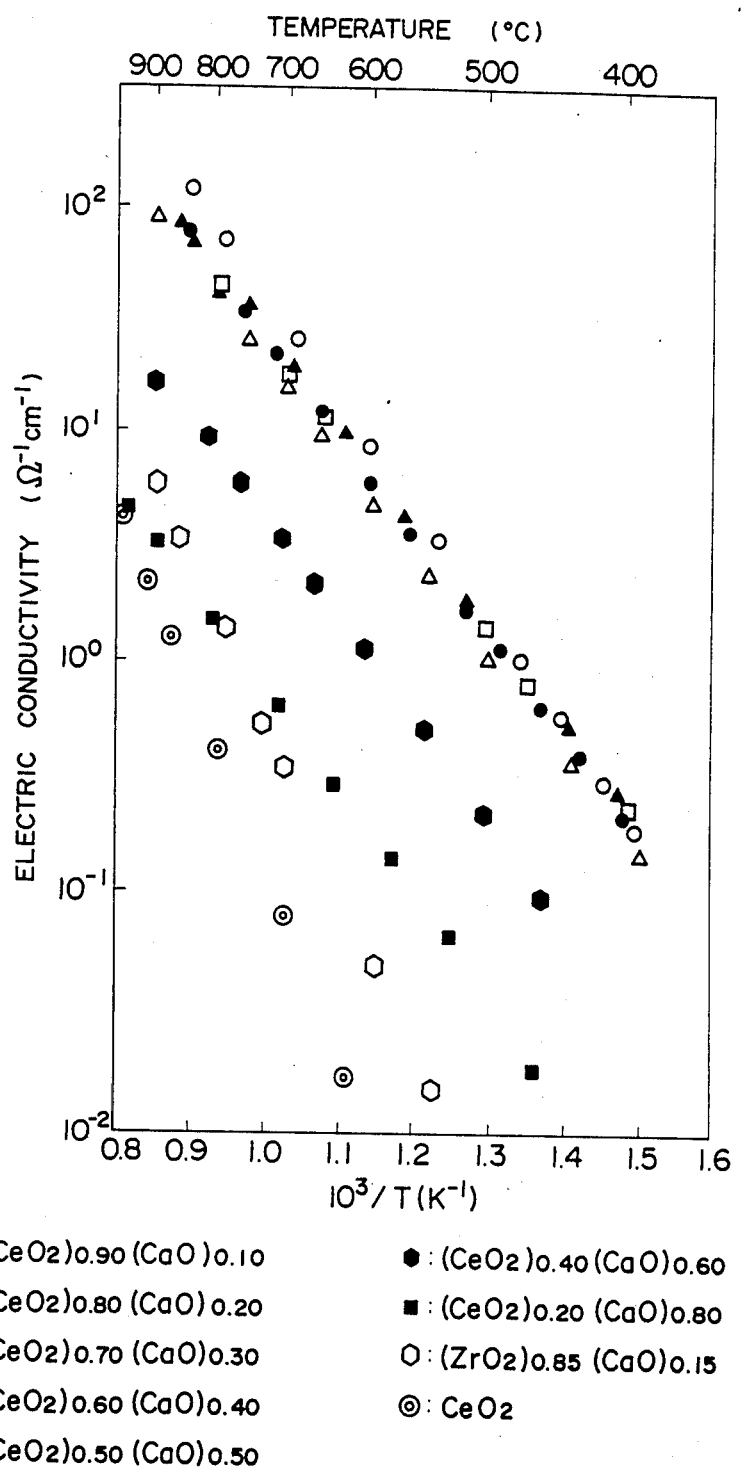

○ : $(CeO_2)_{0.90}(CaO)_{0.10}$     ▲ : $(CeO_2)_{0.80}(CaO)_{0.20}$
□ : $(CeO_2)_{0.70}(CaO)_{0.30}$     ● : $(CeO_2)_{0.60}(CaO)_{0.40}$
△ : $(CeO_2)_{0.50}(CaO)_{0.50}$     ⬣ : $(CeO_2)_{0.40}(CaO)_{0.60}$
■ : $(CeO_2)_{0.20}(CaO)_{0.80}$     ⌀ : $(ZrO_2)_{0.85}(CaO)_{0.15}$
⊙ : $CeO_2$

■ : $(CaO)_{0.50}(CeO_2)_{0.50}$

○ : $(CaO)_{0.50}(CeO_2)_{0.45}(MgO)_{0.05}$

● : $(CaO)_{0.50}(CeO_2)_{0.40}(MgO)_{0.10}$

△ : $(CaO)_{0.50}(CeO_2)_{0.45}(AlO_{1.5})_{0.05}$

▲ : $(CaO)_{0.50}(CeO_2)_{0.40}(AlO_{1.5})_{0.10}$

□ : $(ZrO_2)_{0.89}(CaO)_{0.11}$

MATERIAL OF OXYGEN ION CONDUCTOR

The present invention relates to materials of oxygen ion conductors which have an oxygen ion conductivity higher than that of stabilized zirconia by using $CeO_2$—CaO type oxides and can be applied to fuel cells, sensors and the like.

As a material of oxygen ion conductor, currently there is stabilized zirconia which is already put to practical use as an oxygen sensor and has been investigated for practical use as a material for fuel cells and the like.

The stabilized zirconia is a material wherein CaO, $Y_2O_3$, or $Yb_2O_3$ is added to pure zirconia as a stabilizer because pure zirconia with no stabilizer tends to undergo crystal modification, tetragonal system of fluorite type crystal zirconia in FIG. 1 which is stable at high temperature can be also stable down to low temperatures by the addition of the said oxides producing pores at the same time.

As shown in FIG. 2, the stabilizer is added by about 10–20 mol % which is the range wherein the curve representing the relation between the amount of addition and specific conductance, shows the maximum.

The dependence of specific conductance on temperature and the scopes of ionic conduction of stabilized zirconia are as shown in FIG. 3 and FIG. 4. respectively; the scope of ionic conduction thereof is wide, and the specific conductance thereof is comparatively high, compared with other ion conductors.

However, in the known conventional technology as mentioned above, the temperature at which the stabilized zirconia shows the ionic conduction over a wide oxygen concentration is 600° C. or higher; accordingly, there is a defect that a temperature of 700° C. or higher is necessary when a specific conductance of $0.1\ v\text{-cm}^{-1}$ or higher is required.

BRIEF DESCRIPTION OF THE DRAWINGS

In the accompanying drawings,

In FIG. 4, CSZ is short of Ca-stabilized Zirconia, YDT is short of yttrium dopping thoria;

FIG. 6 is a diagram which shows temperature-dependence of specific conductances of $CeO_2$—CaO binary system oxides and stabilized zirconia in air;

In FIG. 5A,
1 . . . Pt paste electrode,
2 . . . Pt lead wire, and
3 . . . sample;
in FIG. 5B,
101 . . . Pt electrode (Pt mesh),
102 . . . Ag ring,
103 . . . alumina tube,
104 . . . Pt lead wire,
105 . . . sample ($20\phi \times 2$ mm), and
106 . . . thermocouple (CA); and
in FIG. 5C,
201 . . . Pt-paste (Pt mesh),
202 . . . Pt lead wire,
203 . . . current terminal, and
204 . . . voltage terminal.

The object of the present invention is to provide materials of oxygen ion conductors consisting of $CeO_2$—CaO type oxides wherein 5–60 mol %, preferably 10–55 mol % of CaO is mixed with $CeO_2$ having a fluorite structure.

Further object of the present invention is to provide a material of oxygen ion conductor consisting of composite oxides wherein $CeO_2$ in $CeO_2$—CaO type oxides prepared by mixing 5–60 mol % of CaO with $CeO_2$ having a fluorite type structure is replaced by oxide of Mg or Al by 1–20 mol %.

In the $CeO_2$—CaO type oxides mentioned above, from the diagrams of FIG. 6 and FIG. 7 which show the dependence of specific conductances and transport numbers on temperature, the amount of CaO to be combined with $CeO_2$ is 5–60 mol %, preferably 10–50 mol %.

Figure 9:
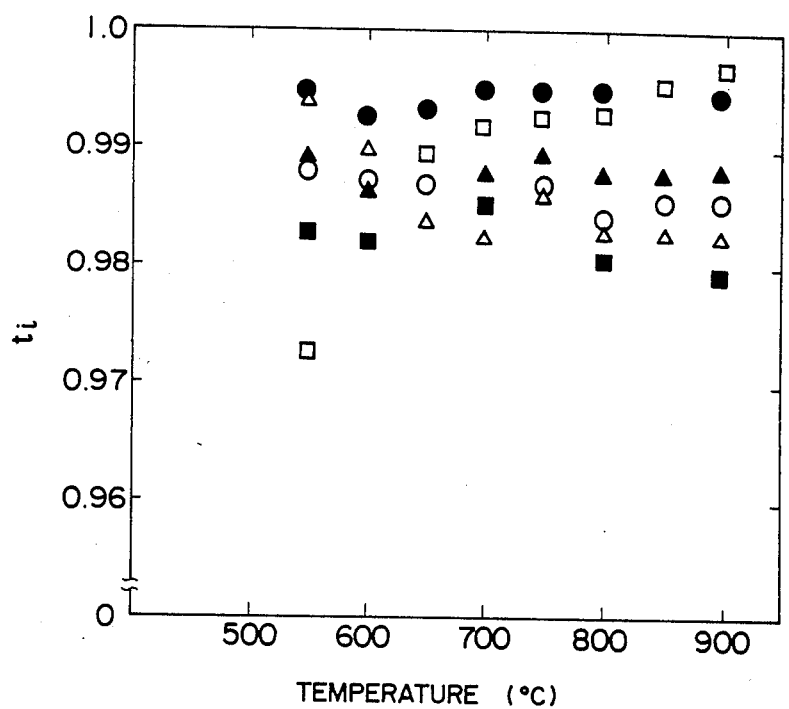
FIG. 9 is a diagram which shows temperature-dependence of transport numbers of composite oxides prepared by adding MgO or $Al_2O_3$ to $CeO_2$—CaO binary system oxides and stabilized zirconia.

Also in the composite oxides prepared by mixing oxide of Mg or Al with $CeO_2$—CaO type oxide, from the diagram in FIG. 9 which shows the dependence of transport numbers on temperature, the added amount of the oxide mentioned above is preferably 5–10 mol %.

Examples will be illustrated herein below to explain the constitution along with the function of the present invention.

EXAMPLE 1

Figure 1:
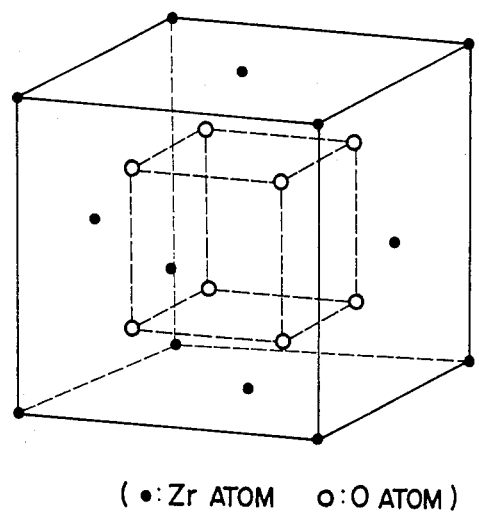
FIG. 1 shows the fluorite type crystal structure of zirconia.
Figure 2:
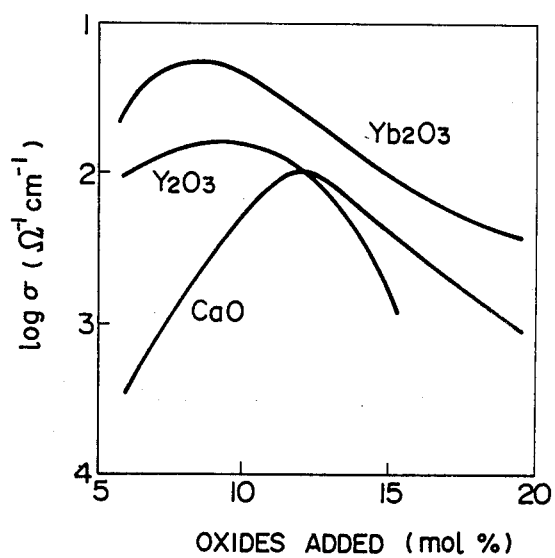
FIG. 2 is a diagram which shows the relation between specific conductance of stabilized zirconia at 800° C. and the amount of addition thereto.
Figure 3:
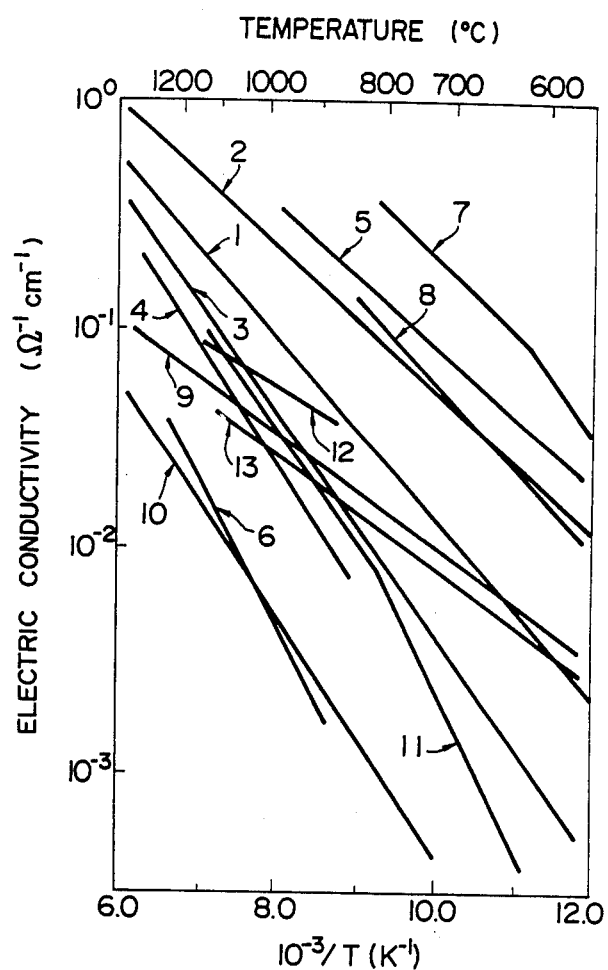
FIG. 3 is a diagram which shows temperature-dependence of specific conductances of oxygen ion conductors.
Figure 4:
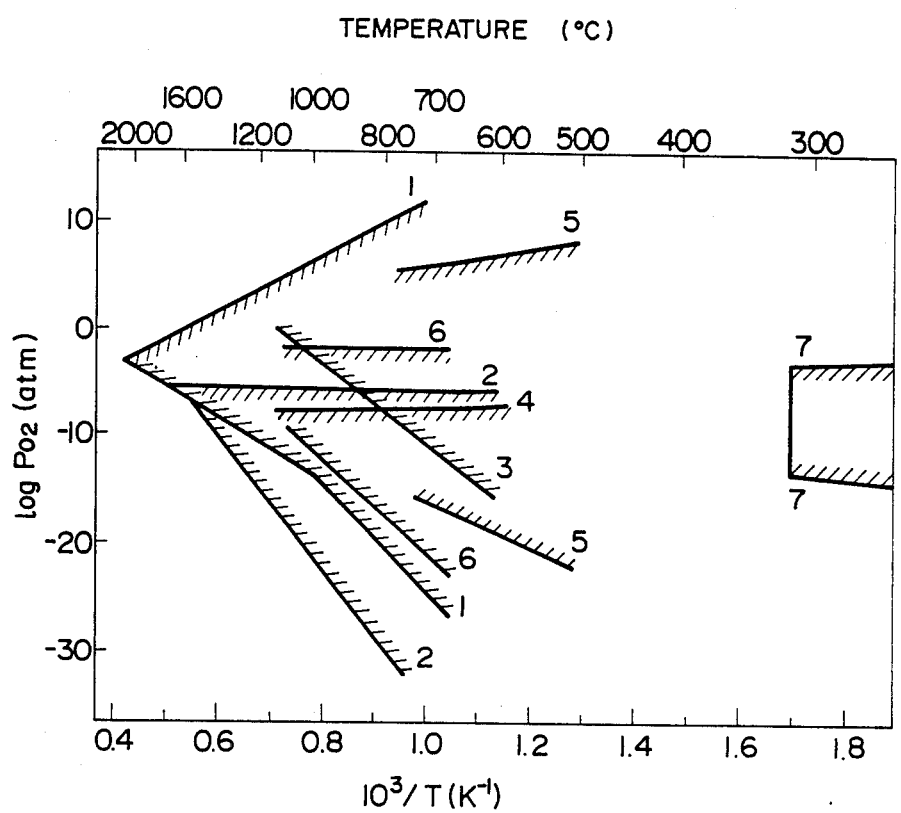
FIG. 4 is a diagram which shows the scopes of ionic conductions of oxygen ion conductors (transport number=1), and in which the inside scopes subjected to hatching show the compositions, respectively.

$CeO_2$—CaO binary system oxide $[CeO_2]_{1-x}[CaO]_x$ (x=0−0.90) having a fluorite type structure as shown in FIG. 1 and showing oxygen ion conductivity was prepared as described below.

Figure 5A:
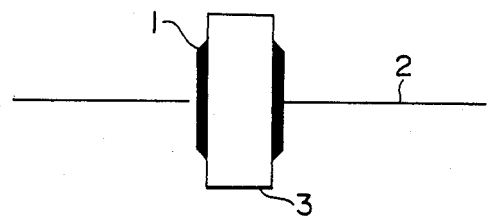
FIG. 5A is schematic diagram which shows geometry of the electrolyte used for the measurement of transport number.
Figure 5B:
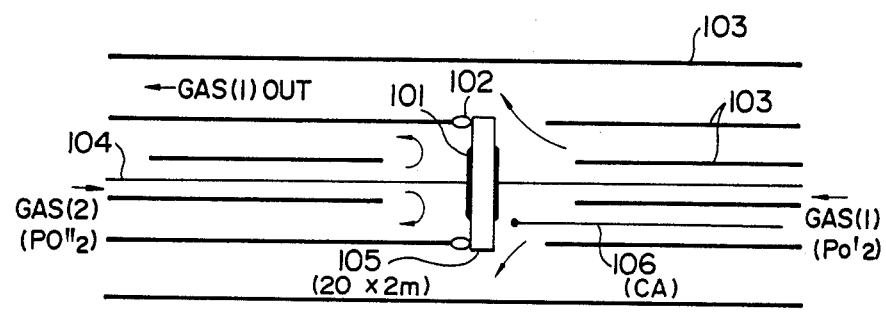
FIG. 5B is a schematic diagram which shows the structure of oxygen concentration cell.

As the starting materials, carbonate salt was used for preparing CaO and cerium oxide, guarantee reagent, for $CeO_2$. The raw materials were obtained by sufficiently drying them at 100°–150° C., weighing appropriate amounts of them, mixing, pulverizing and calcining them at 1300° C. The product was pulverized sufficiently. After obtaining a pellet which measures 20 mm in diameter and 3 to 4 mm in thickness, by molding the pulverized product with a molding die, they were pressed with a hydrostatic press (2.5 tons×1 min) and sintered at 1450° C. for 15 hours. As shown in FIG. 5A, Pt paste was baked on both sides of the pellet to form an electrode having a diameter of about 10 mm, and Pt wire can be adhering as lead wire. Further, as shown in FIG. 5B, the pellet was welded to an alumina-tube, which is a good insulator, by fusion of both Ag metal and Ag paste applied in place to form a galvanic cell. The transport number was measured by the electromotive force of the oxygen concentration cell.

Figure 5C:
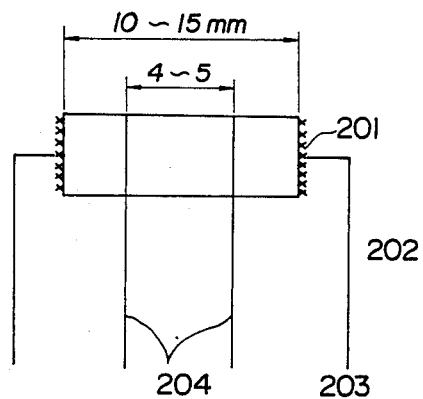
FIG. 5C is a schematic diagram which shows oxide samples for four-terminal measurement.

Also as shown in FIG. 5C, the pellet mentioned above was cut off to form a macromolecular pillar having a side of 3 mm and a length of 10–15 mm and the specific conductance thereof was measured by four-terminal method.

Temperature-dependence of specific conductances ($\delta T$) of $CeO_2$—$CaO$ binary system oxides $[CeO_2]_{1-x}[CaO]_x$ (x=0.00, 0.10, 0.20, 0.30, 0.40, 0.50, 0.60, 0.70, 0.80, and 0.90) and stabilized zirconia was measured by four-terminal method.

$$\delta T = \frac{nA}{k} \exp\left(-\frac{Ea}{kT}\right)$$

wherein
 $\delta$: specific conductance,
 n: number of valence electron (actual number of ions capable of contribution to conduction),
 k: Boltzmann's constant
 A: a constant inherent in the material,
 Ea: activation energy required for the movement of ions, and
 T: absolute temperature.

The results are shown in FIG. 6.

According to FIG. 6, the specific conductance of simple substance $CeO_2$ is smaller than that of stabilized zirconia $[(ZrO_2)_{0.85}(CaO)_{0.15}]$. However, the specific conductances of $CeO_2$—$CaO$ binary system oxides $(CeO_2)_{1-x}(CaO)_x$ (x=0.10, 0.20, 0.30, 0.40, 0.50, 0.60, 0.70, 0.80, and 0.90) which contain CaO therein showed values as high as 100 times that of stabilized zirconia at 600° C. and 15 times, at 900° C.

Accordingly, it was confirmed that the specific conductance thereof at 400° C. shows a value equivalent to that of stabilized zirconia at 700° C.

Also temperature-dependence of transport numbers ($t_i$) of binary system oxides $(CeO_2)_{1-x}(CaO)_x$ (x=0.10, 0.20, 0.30, 0.40, 0.50, 0.60, 0.70, 0.80, and 0.90) and stabilized zirconia was measured by oxygen concentration cell method in accordance with the equation mentioned below.

Figure 7:
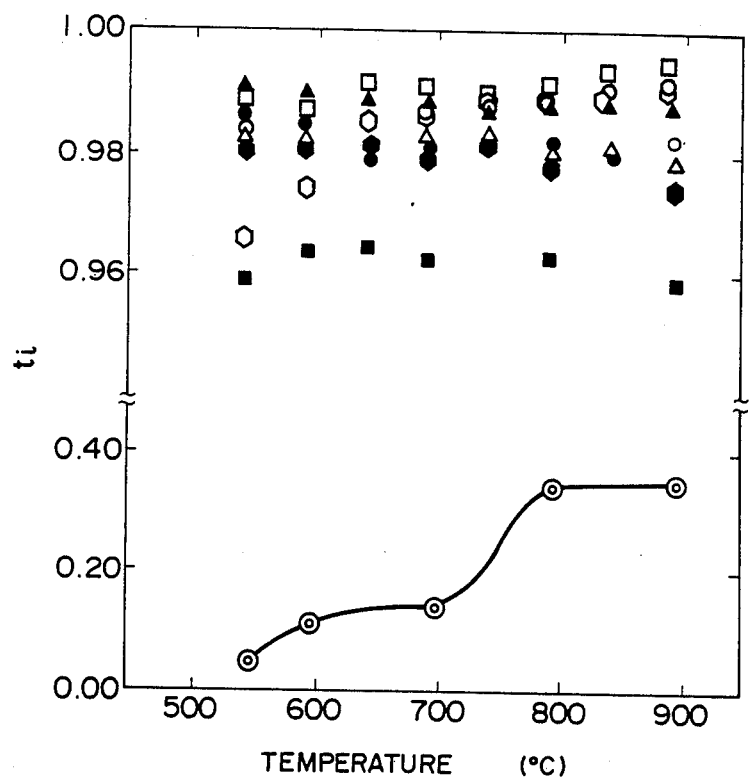
FIG. 7 is a diagram which shows temperature-dependence of transport numbers of $CeO_2$—CaO binary system oxides and stabilized zirconia.

The results are shown in FIG. 7.

$$\text{Transport number } (t_i) = \frac{E_{obs}}{\frac{RT}{4F} \ln \frac{P_{O_2}'}{P_{O_2}''}}$$

wherein
 $E_{obs}$: electromotive force,
 R: gas constant,
 T: absolute temperature,
 F: Faraday constant, and
 $P_{O_2}'$, $P_{O_2}''$: partial pressures of oxygen.

As shown in FIG. 7, though the transport number of simple substance $CeO_2$ is very small, when CaO is mixed therewith, the transport number attains to nearly 1 at a temperature of 550° C. or higher. Consequently, in FIG. 5 and FIG. 6, $CeO_2$—$CaO$ binary system oxides showed oxygen ion conductivities much more excellent than that of stabilized zirconia.

EXAMPLE 2

Oxygen ion conductors of composite oxides wherein $CeO_2$ of $CeO_2$—$CaO$ binary system oxide is replaced by oxide of Mg or Al by 5–10 mol %:
 $(CaO)_{0.5}(CeO_2)_{0.45}(MgO)_{0.05}$,
 $(CaO)_{0.5}(CeO_2)_{0.40}(MgO)_{0.10}$,
 $(CaO)_{0.5}(CeO_2)_{0.45}(AlO_{1.5})_{0.05}$, and
 $(CaO)_{0.5}(CeO_2)_{0.40}(AlO_{1.5})_{0.10}$
were prepared in the same manner as in Example 1 by adding MgO or $Al_2O_3$ to the starting materials in Example 1.

Figure 8:
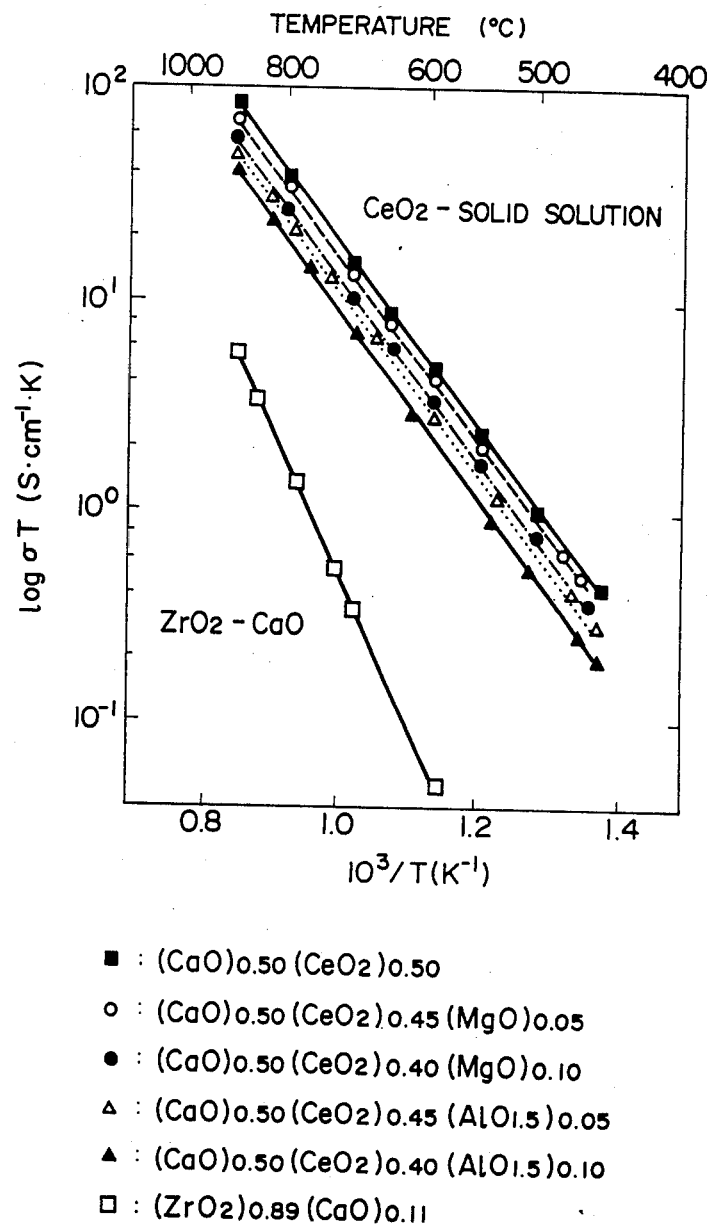
FIG. 8 is a diagram which shows temperature-dependence of conductivities of composite oxides prepared by adding MgO or $Al_2O_3$ to $CeO_2$—CaO binary system oxides and stabilized zirconia.

Temperature-dependence of conductivities of composite oxides prepared by adding MgO or $Al_2O_3$ to $CeO_2$—$CaO$ binary system oxides in FIGS. 8 and 9 and stabilized zirconia $(ZrO_2)_{0.89}(CaO)_{0.11}$ was measured, and the results are shown in FIG. 8 and FIG. 9.

The transport number $t_i$ was obtained at partial pressures of oxygen $P_{O_2}'=1.0$ atm and $P_{O_2}''=0.21\text{-}10^{-3}$ atm in accordance with the Nernst equation in FIG. 9.

From FIG. 8 and FIG. 9, it was found that the temperature-dependence of specific conductances and transport numbers of said oxides is much more excellent than that of stabilized zirconia.

Also it was found that said oxides show characteristics equal to or better than those of $CeO_2$—$CaO$ binary system oxides mentioned afore.

Thus, the advantages of the present invention are as follows:

(1) Since $CeO_2$—$CaO$ type oxides have specific conductances higher than that of stabilized zirconia, by using them for the electrolyte of solid galvanic cells or fuel cells, it is possible to improve in efficiency several dozens times as much in term of specific conductance and lower the functioning temperature, compared with conventional materials.

(2) When they are used as the material for $CeO_2$—$CaO$ system oxide oxygen sensors, the functional temperature thereof is lower than that of conventional stabilized zirconia having a functional temperature of about 600° C. by about 200°–300° C, whereby development of a sensor having a longer life becomes possible.

We claim:

1. Materials of oxygen ion conductors comprising $CeO_2$-$CaO$ binary system oxides in which 20–60 mol % of CaO is mixed with $CeO_2$ having a structure of fluorite crystal.

2. Materials of oxygen ion conductors as in claim 1 further comprising magnesium or aluminum oxides in 1–20 mol %, in a ternary system.

3. Materials as in claim 2 wherein said aluminum or magnesium oxides comprise 5–10% in a ternary system.

4. Materials, as in claim 3 wherein said aluminum or magnesium oxide addition comprises a ternary system comprising 20–60 mol % CaO, 38–70.5 mol % $CeO_2$, and 2–9.5 mol % MgO or $Al_2O_3$.

5. A method for preparing a solid electroyte for use in galvanic cells, fuel cells or oxygen sensors comprising mixing 20–60 mol % of CaO with $CeO_2$, said $CeO_2$ having a structure of fluorite to form a mixture, and pelletizing said mixture.

6. A method for preparing a solid electrolyte for use in galvanic cells, fuels cells or oxygen sensors comprising mixing 20–60 mol % CaO, 38–70.5 mol % $CeO_2$, and 2–9.5 mol % MgO or $Al_2O_3$ to form a mixture and a pelletizing said mixture.

7. Materials of oxygen ion conductors comprising 5–60 mol % of CaO mixed with $CeO_2$ having a fluorite structure, and 1–20 mol % of an oxide of magnesium or aluminum.

* * * * *